United States Patent [19]

Gordon

[11] Patent Number: 4,749,781

[45] Date of Patent: Jun. 7, 1988

[54] AMINOCARBONYL RENIN INHIBITORS

[75] Inventor: Eric M. Gordon, Pennington, N.J.

[73] Assignee: E. R. Squibb & Sons, Inc., Princeton, N.J.

[21] Appl. No.: 909,434

[22] Filed: Sep. 19, 1986

Related U.S. Application Data

[63] Continuation-in-part of Ser. No. 797,321, Nov. 12, 1985, abandoned.

[51] Int. Cl.⁴ .............................................. A61K 37/02
[52] U.S. Cl. .................................. 530/323; 530/328; 530/329; 530/330; 530/331; 530/332
[58] Field of Search ............... 530/323, 328, 329, 330, 530/331, 332; 514/16, 17, 18, 19

[56] References Cited

U.S. PATENT DOCUMENTS

| | | | |
|---|---|---|---|
| 4,470,971 | 9/1984 | Boger et al. | 530/330 |
| 4,477,441 | 10/1984 | Boger et al. | 514/11 |
| 4,478,826 | 10/1984 | Veber et al. | 530/328 |
| 4,479,941 | 10/1984 | Veber et al. | 530/328 |
| 4,485,099 | 11/1984 | Boger et al. | 530/317 |
| 4,514,391 | 4/1985 | Gordon et al. | 514/2 |
| 4,548,926 | 10/1985 | Matsueda et al. | 514/9 |
| 4,616,088 | 10/1986 | Ryono et al. | 546/336 |
| 4,629,724 | 12/1986 | Ryono et al. | 514/18 |
| 4,636,491 | 1/1987 | Bock et al. | 530/300 |
| 4,645,759 | 2/1987 | Luly et al. | 530/331 |
| 4,650,661 | 3/1987 | Szelke et al. | 530/329 |
| 4,657,931 | 4/1987 | Baran et al. | 530/331 |
| 4,661,473 | 4/1987 | Boger et al. | 530/329 |
| 4,663,310 | 5/1987 | Bock et al. | 530/329 |
| 4,665,055 | 5/1987 | Evans | 530/331 |
| 4,665,193 | 5/1987 | Ryono et al. | 548/344 |
| 4,668,663 | 5/1987 | Boger | 530/329 |
| 4,668,769 | 5/1987 | Hoover | 530/331 |
| 4,668,770 | 5/1987 | Boger et al. | 530/331 |
| 4,680,284 | 7/1987 | Luly et al. | 530/331 |

FOREIGN PATENT DOCUMENTS

| | | |
|---|---|---|
| 104041 | 3/1984 | European Pat. Off. |
| 114993 | 8/1984 | European Pat. Off. |
| 128762 | 12/1984 | European Pat. Off. |
| 8403044 | 8/1984 | PCT Int'l Appl. |

*Primary Examiner*—Delbert R. Phillips
*Assistant Examiner*—Nathan M. Nutter
*Attorney, Agent, or Firm*—Lawrence S. Levinson; Stephen B. Davis

[57] ABSTRACT

Compounds of the formula

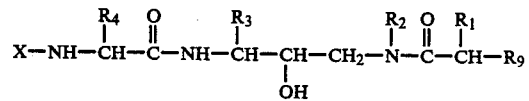

are disclosed. These compounds intervene in the conversion of angiotensinogen to angiotensin II by inhibiting renin and thus are useful as antihypertensive agents.

12 Claims, No Drawings

AMINOCARBONYL RENIN INHIBITORS

RELATED APPLICATION

This application is a continuation-in-part of U.S. Ser. No. 797,321 filed Nov. 12, 1985, now abandoned.

BACKGROUND OF THE INVENTION

Jones et al. in WO No. 84/03044 disclose renin inhibiting tetra-, penta-, or hexapeptide analogues of the formula

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbon-nitrogen link which as such or in hydrated form is an unhydrolyzable tetrahedral analogue of the transition state of the peptide bond as given above. In particular, A is defined as

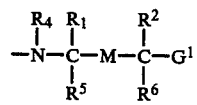

wherein M can be —CH—OH.

Szelke et al. in European patent application No. 104,041 disclose renin inhibitory polypeptides including the partial sequence

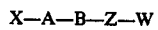

and

wherein A is

and G is

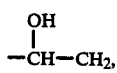

X is hydrogen, protecting group, or an amino acyl residue, B is a lipophilic amino acyl residue, and Z plus W are an amino alcohol residue or Z is aminoacyl and W is hydroxy, ester, amide, etc.

Matsueda et al. in European patent application No. 128,672 disclose renin inhibiting peptides of the formula

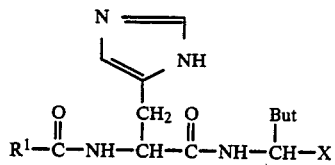

wherein But represents an isobutyl or sec-butyl group and X includes a group of the formula —CH($R^2$)—Y.

Gordon et al. in U.S. Pat. No. 4,514,391 disclose hydroxy substituted peptide compounds of the formula

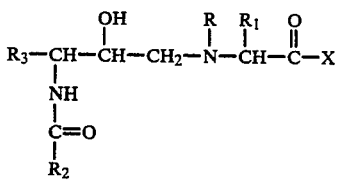

which possess angiotensin converting enzyme or enkephalinase inhibition activity.

SUMMARY OF THE INVENTION

This invention is directed to new amino carbonyl containing renin inhibitors of formula I including pharmaceutically acceptable salts thereof

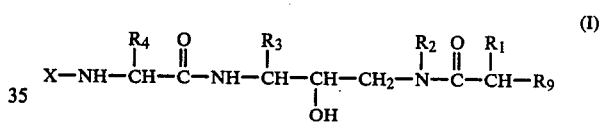

X is

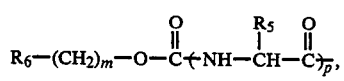

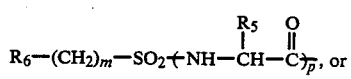

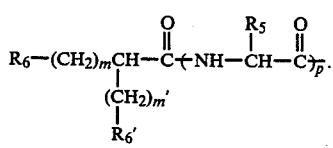

$R_3$, $R_4$, $R_5$, $R_{11}$, and $R_{12}$ are independently selected from hydrogen, lower alkyl, halo substituted lower alkyl, —$(CH_2)_n$-aryl, —$(CH_2)_n$-heterocyclo, —$(CH_2)_n$—OH, —$(CH_2)_n$—$NH_2$, —$(CH_2)_n$—SH, —$(CH_2)_n$—S-lower alkyl, —$(CH_2)_n$—S—$(CH_2)_g$—$NH_2$, —$(CH_2)_n$—O—$(CH_2)_g$—OH, —$(CH_2)_n$—O—$(CH_2)_g$—$NH_2$, —$(CH_2)_n$—S—$(CH_2)_g$—OH,

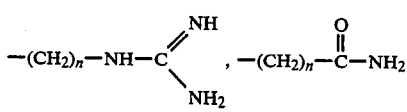

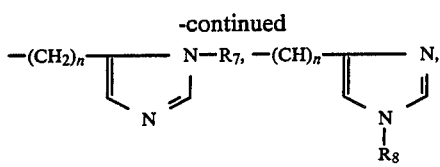

and —(CH$_2$)$_n$-cycloalkyl.

R$_1$ and R$_2$ are independently selected from hydrogen, lower alkyl, —(CH$_2$)$_m$-aryl, and —(CH$_2$)$_m$-cycloalkyl and —(CH$_2$)$_n$-heterocyclo. R$_6$ and R$_6'$ are independently selected from lower alkyl, cycloalkyl, aryl, and heterocyclo. p is zero or one. m and m' are independently selected from zero and an integer from 1 to 5. n is an integer from 1 to 5. g is an integer from 2 to 5.

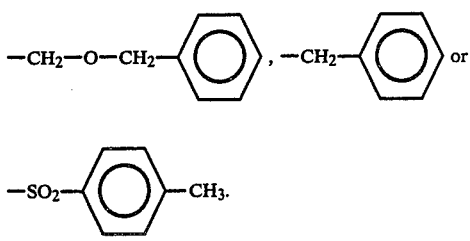

R$_8$ is 2,4-dinitrophenyl. R$_9$ is hydrogen, lower alkyl, —(CH$_2$)$_m$-cycloalkyl, —(CH$_2$)$_m$-aryl, —(CH$_2$)$_n$-heterocyclo,

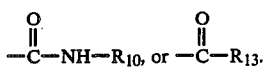

R$_{10}$ is hydrogen, lower alkyl, —(CH$_2$)$_m$-cycloalkyl, —(C$_2$)$_m$-aryl, —(C$_2$)$_n$-heterocyclo, or

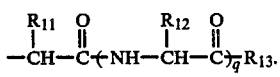

q is zero or one. R$_{13}$ is hydroxy, —O-lower alkyl, —O—(CH$_2$)$_m$-cycloalkyl, —O—(CH$_2$)$_m$-aryl, —O—(CH$_2$)$_n$-heterocyclo, —NH$_2$, or —O-salt forming ion.

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one to four N atoms, or one O and up to two N atoms, or one S and up to two N atoms. The heterocyclo ring is attached by way of an available carbon atom. Preferred heterocyclo groups include 2- and 3-thienyl, 2- and 3-furyl, 2-, 3- and 4-pyridyl, and imidazolyl. The term heterocyclo also includes bicyclic rings wherein the five or six membered ring containing O, S and N atoms as defined above is fused to a benzene ring. The preferred bicyclic ring is indolyl.

The compounds of formula I wherein X is

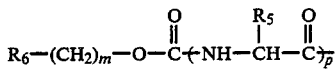

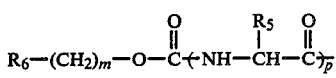

can be prepared by coupling an alcohol of the formula

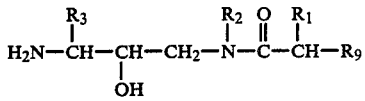

preferably the hydrochloride salt thereof with a peptide of the formula

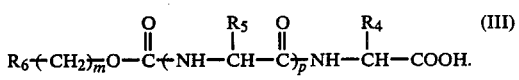

This reaction is preferably performed in a solvent such as dimethylformamide and in the presence of hydroxybenzotriazole, diisopropylethylamine, and a coupling agent such as dicyclohexylcarbondiimide.

The corresponding compounds of formula I wherein p is zero can be prepared by coupling the alcohol of formula II with the amino acid of the formula

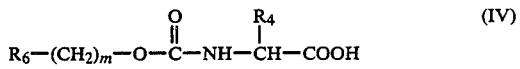

to yield the products of the formula

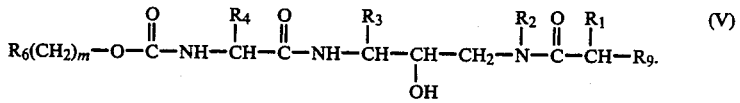 (V)

When $R_6$ is t-butyl or benzyl, then the product of formula V can be treated so as to remove the t-butoxycarbonyl or benzyloxycarbonyl group such as by the use of hydrochloric acid when $R_6$ is t-butyl to yield the amine of the formula

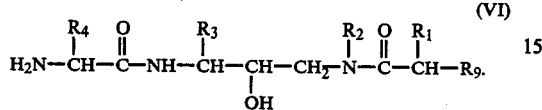 (VI)

Coupling with the amino acid of the formula

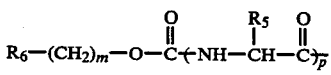 (VII)

yields the products of formula I wherein p in one.

The compounds of formula I wherein X is other than

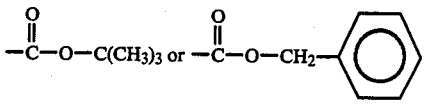

can be prepared by treating the product of formula I wherein $R_6$ is

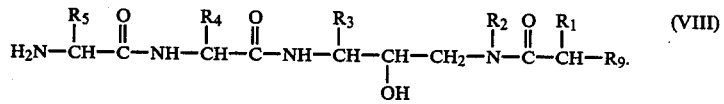

and m is zero to remove the t-butyoxycarbonyl or benzyloxycarbonyl group and yield the intermediates of the formula

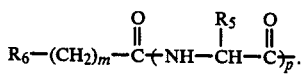 (VIII)

The amine of formula VIII or VI is treated with the acid chloride of the formula

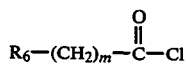 (IX)

in the presence of triethylamine to yield the products of formula I wherein

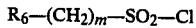

The amine of formula VIII or VI is treated with the substituted sulfonyl chloride of the formula $R_6$—$(CH_2)_m$—$SO_2$—Cl   (X)

to yield the products of formula I wherein X is

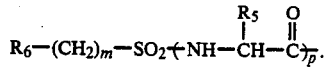

The products of formula I wherein X is

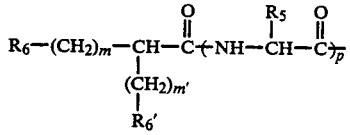

can be prepared by coupling the carboxylic acid of the formula

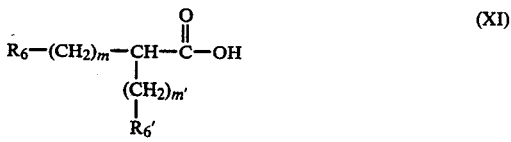 (XI)

to the amine of formula VIII or VI in the presence of dicyclohexylcarbodiimide and 1-hydroxybenzotriazole hydrate. Alternatively, the acid of formula XI can be converted to the acid chloride and this acid chloride can then be coupled to the amine of formula VIII or VI in the presence of triethylamine and tetrahydrofuran or water and sodium bicarbonate.

When $R_2$ is hydrogen, the alcohol of formula II can be prepared as follows. A chloromethylketone of the formula (XII)

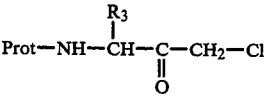

is treated with a conventional reducing agent such as sodium borohydride, diisobutyl aluminum hydride, lithium tri t-butoxy aluminum hydride, etc., wherein Prot is a amino protecting group such as t-butoxycarbonyl, to give the chloromethyl compound of the formula

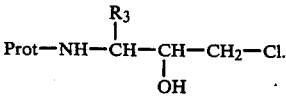 (XIII)

Treatment with sodium hydride gives the epoxide of the formula

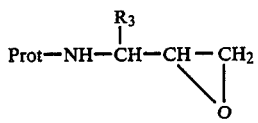 (XIV)

which is then treated with ammonia/methanol solution to give the aminomethyl alcohol of the formula

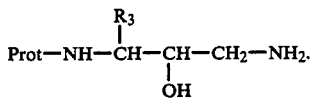 (XV)

The carboxylic acid of the formula

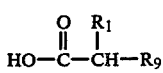 (XVI)

is coupled to the aminomethyl alcohol of formula XV to give the alcohol of the formula

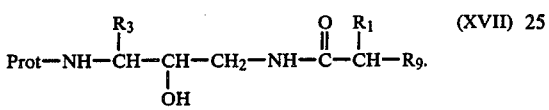 (XVII)

This reaction is performed in the presence of hydroxybenzotriazole hydrate and a coupling agent such as dicyclohexylcarbodiimide. Alternatively, the acid of formula XVI can be converted to its acid chloride or other activated form which can then be used to acylate the aminomethyl alcohol of formula XV and give the alcohol of formula XVII.

The alcohol of formula XVII is treated to remove the Prot group such as by treatment with hydrochloric acid when Prot is t-butoxycarbonyl and give the alcohol of formula II.

When $R_2$ is other than hydrogen, the epoxide of formula XIV is treated with the amine of the formula $$H_2N-R_2 \qquad (XVIII)$$

followed by treatment with the acid or activated form of the acid of formula XVI to give the corresponding alcohol of formula XVII wherein $R_2$ is other than hydrogen. The Prot group is removed as described above to give the alcohol of formula II.

The alcohol of formula II wherein $R_3$ is cyclohexylmethyl can be prepared by treating the aminomethyl alcohol of formula XV wherein $R_3$ is benzyl with platinum oxide. The resulting cyclohexylmethyl compound is then reacted with the acid or activated form of the acid of formula XVI as described above.

In the above reactions, if any of $R_1$, $R_2$, $R_3$, $R_4$, $R_5$, $R_{11}$ or $R_{12}$ are —$(CH_2)_n$-aryl wherein aryl is phenyl, 1-naphthyl, 2-naphthyl substituted with one or more hydroxy or amino groups, —$(CH_2)_n$-heterocyclo wherein heterocyclo is an imidazolyl, —$(CH_2)_n$—$NH_2$, —$(CH_2)_n$—SH, —$(CH_2)_n$—OH, or

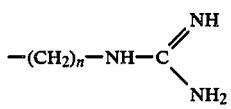

then the hydroxyl, amino, imidazolyl, mercaptan, or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, The Peptides, Volume 1, "Major Methods Of Peptide Bond Formation", Academic Press (1979).

Preferred compounds of this invention are those of formula I wherein:

X is lower

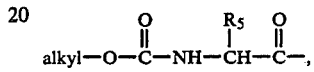

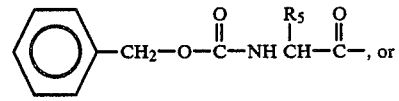

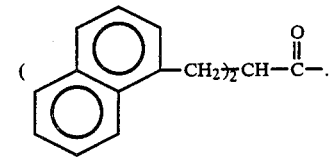

$R_1$ is hydrogen or lower alkyl of 1 to 5 carbons.

$R_2$ is hydrogen, lower alkyl of 1 to 5 carbons, —$(CH_2)_m$-cyclopentyl, or —$(CH_2)_m$-cyclohexyl, or

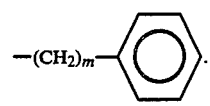

m is an integer from 1 to 3.

$R_3$ is lower alkyl of 3 to 5 carbons, —$CH_2$-cyclopentyl, —$CH_2$-cyclohexyl or

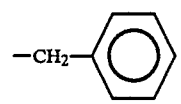

$R_4$ is

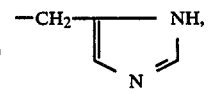

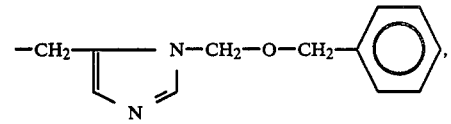

-continued $-CH_2-\text{(indole)}$, $-CH_2-\text{(phenyl)}$, $-CH_2-\text{(phenyl)}-OH$, $-CH_2-\text{(pyridyl)}$, $-CH_2-\text{(pyridyl)}$, $-CH_2-\text{(pyridyl)}$, $-(CH_2)_2-\text{(phenyl)}$, or $-CH_2-\text{(imidazolyl-2,4-dinitrophenyl)}$ $R_5$ is $-CH_2-\text{(phenyl)}$, $-(CH_2)_2-\text{(phenyl)}$, $-CH_2-(\alpha\text{-naphthyl})$, $-CH_2-(\beta\text{-naphthyl})$, $-CH_2-\text{(phenyl)}-OH$, $-CH_2\text{-cyclopentyl}$, $-CH_2\text{-cyclohexyl}$, $-CH_2-\text{(pyridyl)}$, $-CH_2-\text{(pyridyl)}$, $-CH_2-\text{(pyridyl)}$, $-CH_2-\text{(imidazolyl)}$, or $-CH_2-\text{(indole)}$.

$R_9$ is lower alkyl of 1 to 5 carbons, $-(CH_2)_m$-cyclopentyl, $-(CH_2)_m$-cyclohexyl, $-(CH_2)_m-\text{(phenyl)}$, $-(CH_2)_n-\text{(pyridyl)}$, or $$-\overset{O}{\underset{\|}{C}}-NH-R_{10}.$$

$R_{10}$ is lower alkyl of 1 to 5 carbons, $-(CH_2)_m$-cyclopentyl, $-(CH_2)_m$-cyclohexyl, $-(CH_2)_m-\text{(phenyl)}$ or $-(CH_2)_n-\text{(pyridyl)}$.

n is an integer from 1 to 3.

Most preferred are the above compounds wherein X is $$(H_3C)_3-C-O-\overset{O}{\underset{\|}{C}}-NH-\overset{R_5}{\underset{|}{CH}}-\overset{O}{\underset{\|}{C}}-.$$

$R_1$ is hydrogen or $-(CH_2)_3-CH_3$.
$R_2$ is hydrogen, $-(CH_2)_4-CH_3$, or $-CH_2-\text{(phenyl)}$.

$R_3$ is $-CH_2CH(CH_3)_2$ or $-CH_2$-cyclohexyl.
$R_4$ is $-CH_2-\text{(imidazolyl)}-NH$.

$R_5$ is $-CH_2-\text{(phenyl)}$ $R_9$ is $-(CH_2)_2-CH_3$, $-CH_2-\text{(phenyl)}$, or $-\overset{O}{\underset{\|}{C}}-NH-CH_2-\text{(phenyl)}$.

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I wherein $R_9$ is

or $R_{10}$ is

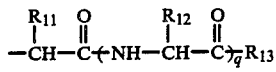

and $R_{13}$ is hydroxy form acid addition salts when treated with a salt forming ion. Suitable salt forming ions include alkali metal salt ions such as sodium and potassium and alkaline earth metal salt ions such as calcium and lithium.

The compounds of formula I contain asymmetric centers when any or all of $R_3$, $R_4$, $R_5$, $R_{11}$, and $R_{12}$ are other than hydrogen and at the carbon to which the —OH group is attached. Thus, the compounds of formula I can exist in diasteroisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg., preferably about 250 to 500 mg. per kg. of body weight per day is appropriate to reduce blood pressure. The substance is preferably administered orally, but parenteral routes such as the subcutaneous, intramuscular, intraveneous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg., preferably about 3000 to 4000 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

$N^2$-[N-[(1,1-Dimethylethoxy)carbonyl]-L-phenylalanyl]-N-[1-[1-hydroxy-2-[(1-oxopentyl)amino]ethyl]-3-methylbutyl]-L-histidinamide (a)
(S)-[3-Methyl-1-(3-chloro-2-hydroxypropyl)butyl]carbamic acid, 1,1-dimethylethyl ester Sodium borohydride (1.9 g., 50 mmole) is added to a solution of (S)-[3-methyl-1-[(chloromethyl)carbonyl]butyl]carbamic acid, 1,1-dimethylethyl ester (5.3 g., 20 mmole) in tetrahydrofuran/water (50 ml./10 ml.) at 0° with stirring. After 2 hours the reaction mixture is quenched with 10% potassium bisulfate, diluted with ethyl acetate (250 ml.), washed with water (twice), saturated sodium bicarbonate (twice), and 10% potassium bisulfate (twice), dried over sodium sulfate, and concentrated to give 5.0 g. of white solid (S)-[3-methyl-1-(3-chloro-2-hydroxypropyl)butyl]carbamic acid, 1,1-dimethylethyl ester; m.p. (63°) 93–96°.

(b) (S)-[3-Methyl-1-(2,3-epoxypropyl)butyl]carbamic acid, 1,1-dimethylethyl ester Sodium hydride (0.74 g., 18.6 mmole) is added to a solution of (S)-[3-methyl-1-(3-chloro-2-hydroxypropyl)butyl]carbamic acid, 1,1-dimethylethyl ester (5.0 g., 18.6 mmole) in tetrahydrofuran (50 ml., distilled). After stirring overnight at room temperature, the reaction mixture is filtered and the filtrate concentrated. The oily residue is redissolved in ether, filtered and concentrated to give 4.09 g. of (S)-[3-methyl-1-( 2,3-epoxypropyl)butyl]carbamic acid, 1,1-dimethylethyl ester as a colorless oil. TLC (silica gel; ethyl acetate/hexane, 1:4) $R_f$=0.46.

(c)
(1S)-[3-Methyl-1-(3-amino-2-hydroxypropyl)butyl]carbamic acid, 1,1-dimethylethyl ester (S)-[3-Methyl-1-(2,3-epoxypropyl)butyl]carbamic acid, 1,1-dimethylethyl ester (3.6 g., 15.7 mmole) is added to a solution of saturated ammonia/methanol (100 ml.) and stirred for 36 hours at room temperature. The reaction mixture is concentrated into a solid residue of 3.8 g. of (1S)-[3-methyl-1-(3-amino-2-hydroxypropyl)butyl]carbamic acid, 1,1-dimethylethyl ester; m.p. (76°) 90–92°.

(d)
N-[(3S)-3-[[(1,1-Dimethylethoxy)carbonyl]amino]-2-hydroxy-5-methylhexyl]pentanamide To a solution of (1S)-[3-methyl-1-(3-amino-2-hydroxypropyl)butyl]carbamic acid, 1,1-dimethylethyl ester (1.9 g., 7.7 ml.) in tetrahydrofuran (50 ml., distilled) at 0° is added 1N sodium hydroxide (38.5 ml., 38.5 mmole) and a solution of valeryl chloride (2.74 ml., 23.1 mmole) in tetrahydrofuran (20 ml., distilled). After stirring for 2 hours (0°→room temperature), the reaction mixture is diluted with ethyl acetate (250 ml.) and washed with water (twice), saturated sodium bicarbonate (twice), and 10% potassium bisulfate (twice), dried over sodium sulfate, and concentrated into a colorless oil (2.4 g.). Purification by flash chromatography (Whatman LPS-1 silica gel, eluting with ethyl acetate:hexane, 1:1) gives 1.0 g. of N-[(3S)-3-[[(1,1-dimethylethoxy)carbonyl]amino]-2-hydroxy-5-methylhexyl]pentanamide as a colorless oil. TLC (silica gel; ethyl acetate:hexane, 4:1) $R_f = 0.41$.

(e)
N-[(3S)-3-Amino-2-hydroxy-5-methylhexyl]pentanamide, monohydrochloride

A solution of N-[(3S)-3-[[(1,1-dimethylethoxy)carbonyl]amino]-2-hydroxy-5-methylhexyl]pentanamide (1.0 g., 3.0 mmole) in saturated hydrochloric acid/ethyl acetate (50 ml.) is stirred at 0° for 3 hours. The reaction mixture is concentrated into a hygroscopic solid residue. Trituration with ether gives 0.66 g. of N-[(3S)-3-amino-2-hydroxy-5-methylhexyl]pentanamide, monohydrochloride as a white foam; m.p. 37–39°. TLC (silica gel; 2% NH₄OH-n-propanol) $R_f = 0.38$ Anal. calc'd. for $C_{12}H_{26}N_2O_2 \cdot HCl \cdot 0.38 H_2O$:
C, 52.68; H, 10.22; N, 10.24; Cl, 12.91 Found: C, 52.68; H, 10.23; N, 10.24; Cl, 12.96.

(f)
N-[N-[(1,1-Dimethylethoxy)carbonyl]-L-phenylalanyl]-1'-[(phenylmethoxy)methyl]-L-histidine Thionyl chloride (27.2 ml., 375 mmole) is added in drops to a stirred solution in an icebath of L-histidine (38.75 g., 240 mmole) in methanol (500 ml.). After 15 minutes the ice-bath is removed and the reaction mixture is stirred at room temperature for one hour. After refluxing for 48 hours, it is concentrated in vacuo. The separated crystals are filtered using methanol for washings to 48.93 g. of L-histidine, methyl ester, dihydrochloride. The methanolic solution on dilution with ether affords an additional 10 g. of product; m.p. 208–209°; $[\alpha]_D^{22} = +10.1°$ (c=1.8, water).

Triethylamine (28 ml., 200 ml.) and di-tertbutyl dicarbonate (48 g., 220 mmole) are added to a suspension of L-histidine, methyl ester (24.2 g., 100 mmole) in methanol (80 ml.). After 3.5 hours, the mixture is filtered and the methanolic solution is concentrated in vacuo. The residue is taken into chloroform and washed with 10% citric acid. The crude product on crystallization from isopropyl ether affords 23.1 g. of N,1'-bis[(1,1-dimethylethoxy)carbonyl]-L-histidine, methyl ester; m.p. (62) 88–95°; $[\alpha]_D^{22} = +25.4°$ (c=1.1, carbon tetrachloride).

Benzylchloromethyl ether (11.6 ml., 83.6 mmole) is added to a solution of N,1'-bis[(1,1-dimethylethoxy)carbonyl]-L-histidine, methyl ester (24.7 g., 66.9 mmole) in dry methylene chloride (156 ml.) and the reaction mixture is stirred at room temperature for 5 hours. After concentrating in vacuo and on dissolution in ethyl acetate 17.85 g. of N-[(1,1-dimethylethoxy)carbonyl]-1'-[(phenylmethoxy)methyl]-L-histidine, methyl ester, monohydrochloride crystallizes out; m.p. (148°) 152–153°; $[\alpha]_D^{22} = -19.5°$ (c=1.8, methanol). This methyl ester product is dissolved in hydrogen chloride in acetic acid solution (60 ml., 1.5 N and kept at room temperture for 15 minutes. It is then evaporated in vacuo and the residue is dissolved in hot isopropanol. After cooling, the separated crystals are filtered to yield 7.08 g. of 1-[(phenylmethoxy)methyl]-L-histidine, methyl ester, dihydrochloride; m.p. (170) 173–174°.

1-[(Phenylmethoxy)methyl]-L-histidine, methyl ester, dihydrochloride (1.79 g., 4.94 mmole), 1-hydroxybenzotriazole (0.756 g., 4.94 mmole), and N-(1,1-dimethylethoxy)carbonyl]-L-phenylalanine (1.31 g., 4.94 mmole) are dissolved in dimethylformamide (16 ml.). While stirring the above solution in an ice-bath, dicyclohexylcarbodiimide (1.02 g., 4.94 mmole) and N,N-diisopropylethylamine (1.72 ml., 10 mmole) are added. After 3 hours the ice-bath is removed and the reaction mixture is stirred at room temperature overnight. It is then concentrated to dryness and the residue is triturated with ethyl acetate. The separated urea is filtered off. The ethyl acetate solution is washed with saturated sodium bicarbonate and then it is evaporated. The residue upon crystallization from ethyl acetate gives 1.97 g. of N-[N-[(1,1-dimethylethoxy)carbonyl]-L-phenylalanyl]-1'-[(phenylmethoxy)methyl]-L-histidine, methyl ester; m.p. (165) 166–168°.

N-[N-[(1,1-Dimethylethoxy)carbonyl]-L-phenylalanyl]-1'-[(phenylmethoxy)methyl]-L-histidine, methyl ester (4.5 g., 8.4 mmole) is dissolved in hot methanol (25 ml.). After cooling to room temperature aqueous sodium hydroxide solution (9.24 ml., 1N) is added and the mixture is stirred at room temperature for 3 hours. It is then concentrated in vacuo and water (60 ml.) is added to the residue. After cooling the aqueous solution in an ice-bath, it is acidified to pH 4.5 using aqueous hydrochloric acid. It is then extracted with ethyl acetate to yield 3.95 g. of crystalline N-[N-[(1,1-dimethylethoxy)carbonyl]-L-phenylalanyl]-1'-[(phenylmethoxy)methyl]-L-histidine; m.p. 193–194°; $[\alpha]_D^{22} = -4.8°$ (c=1.1, dimethylformamide).

(g)
N²-[N-[(1,1-Dimethylethoxy)carbonyl]-L-phenylalanyl]-1'-[(phenylmethoxy)methyl]-N-[1-[1-hydroxy-2-[(1-oxopentyl)amino]ethyl]-3-methylbutyl]-L-histidinamide To a cold (0°) solution of N-[(3S)-3-amino-2-hydroxy-5-methylhexyl]pentanamide, monohydrochloride (66.1 mg., 0.25 mmole) in 10 ml. of dimethylformamide is added diisopropylethylamine (0.043 ml., 0.25 mmole), N-[N-[(1,1-dimethylethoxy)carbonyl]-L-phenylalanyl]-1'-[(phenylmethoxy)methyl]-L-histidine (130 mg., 0.25 mmole), 1-hydroxybenzotriazole hydrate (380 mg., 0.25 mmole) and dicyclohexylcarbodiimide (51 mg., 0.25 mmole). After stirring overnight (0°→room temperature), the reaction mixture is diluted with ethyl acetate and washed with water (twice) and saturated sodium bicarbonate (twice), dried over sodium sulfate, and concentrated to give 185 mg. of N²-[N-[(1,1-dimethylethoxy)carbonyl]-L-phenylalanyl]-1'-[(phenylmethoxy)methyl]-N-[1-[1-hyroxy-2-[(1- oxopentyl)amino]ethyl]-3-methylbutyl]-L-histidinamide as a white solid.

(h) N$^2$-[N-[(1,1-Dimethylethoxy)carbonyl]-L-phenylalanyl]-N-[1-[1-hydroxy-2-[(1-oxopentyl)amino]ethyl]-3-methylbutyl]-L-histidinamide A solution of the product from part (g) (175 mg., 0.23 mmole) in methanol (50 ml.) containing palladium hydroxide on carbon catalyst (50 mg.) is hydrogenated overnight. The reaction mixture is filtered and the filtrate is concentrated. The solid residue is triturated with ether to give 120 mg. of white solid N$^2$-[N-[(1,1-dimethylethoxy)carbonyl]-L-phenylalanyl]-N-[1-[1-hydroxy-2-[(1-oxopentyl)amino]ethyl]-3-methylbutyl]-L-histidinamide; m.p. (145°) 150–155°. TLC (silica gel; 15% methanol/chloroform) R$_f$=0.43, with a minor spot at R$_f$=0.78.

Anal. calc'd. for C$_{32}$H$_{50}$N$_6$O$_6$·2.89 H$_2$O: C, 57.64; H, 8.43; N, 12.60 Found: C, 57.64; H, 8.14; N, 12.22.

EXAMPLE 2

N$^2$-[N-(1,1-Dimethylethoxy)carbonyl]-L-phenylalanyl]-1'-(phenylmethoxy)methyl]-[N-(S)-1-[1-hydroxy-2-[(1-oxo-3-phenylpropyl)amino]ethyl]-3-methylbutyl]-L-histidinamide (a) N-[(3S)-3-[[(1,1-Dimethylethoxy)carbonyl]amino]-2-hydroxy-5-methylhexyl]phenpropylamide To a solution of (S)-[3-methyl-1-(3-amino-2-hydroxypropyl)butyl]carbamic acid, 1,1-dimethylethyl ester (1.0 g., 4.5 mmole) in tetrahydrofuran (50 ml., distilled) is added hydrocinnamic acid (0.67 g., 4.5 mmole), 1-hydroxybenzotriazole hydrate (0.69, 4.5 mmole), and dicyclohexylcarbodiimide (0.93 g., 4.5 mmole). After stirring overnight, the reaction mixture is filtered and the filtrate is concentrated. The residue is redissolved in ethyl acetate (75 ml.), washed with saturated sodium bicarbonate (twice), 10% potassium bisulfate (twice), and saturated sodium chloride, dried over sodium sulfate, and concentrated into a semi-solid residue (1.8 g.). Purification by flash chromatography (Whatman silica gel LPS-1, eluting with ethyl acetate: hexane, 3:1) gives 0.88 g. of N-[(3S)-3-[[(1,1-dimethylethoxy)carbonyl]amino]-2-hydroxy-5-methylhexyl]phenpropylamide as a colorless oil.

(b) N-[(3S)-3-Amino-2-hydroxy-5-methylhexyl]phenpropylamide, monohydrochloride

A solution of N-[(3S)-3-[[(1,1-dimethylethoxy)carbonyl]amino]-2-hydroxy-5-methylhexyl]phenpropylamide (0.88 g., 2.33 mmole) in saturated hydrochloric acid/ethyl acetate (25 ml.) is stirred at 0° for 2 hours. The reaction mixture is concentrated to a solid residue. Trituration with ether gives 0.73 g. of N-[(3S)-3-amino-2-hydroxy-5-methylhexyl]phenpropylamide, monohydrochloride.

(c) N$^2$-N-[(1,1-Dimethylethoxy)carbonyl]-L-phenylalanyl]-1'-(phenylmethoxy)methyl]-N-[(S)-1-[1-hydroxy-2-[(1-oxo-3-phenylpropyl)amino]ethyl]-3-methylbutyl]-L-histidinamide To a cold (0°) solution of N-[(3S)-3-amino-2-hydroxy-5-methylhexyl]phenpropylamide, monohydrochloride (0.73 g., 2.33 mmole) in dimethylformamide (25 ml.) is added diisopropylethylamine (0.40 ml., 2.33, mmole), N-[N-[(1,1-dimethylethoxy)carbon[-L-phenylalanyl]-1'-[(phenylmethoxy)methyl]-L-histidine (1.22 g., 2.33 mmole), 1-hydroxybenzotriazole hydrate (0.36 g., 2.33 mmole), and dicyclohexylcarbodiimide (0.48 g., 2.33 mmole). After stirring overnight (0°→room temperature), the reaction mixture is diluted with ethyl acetate (150 ml.), washed with water (twice) and saturated sodium bicarbonate (twice), dried over sodium sulfate and concentrated. The crude product (1.5 g., white solid) is recrystallized from methanol/hexane to give 1.07 g. of N$^2$-[N-[(1,1-dimethylethoxy)-carbonyl]-L-phenylalanyl]-1'-[(phenylmethoxy)methyl]-N-[(S)-1-[1-hydroxy-2-[(1-oxo-3-phenylpropyl)amino[ethyl]-3-methylbutyl]-L-histidinamide a white solid; m.p. (105°). 145°–150°. TLC (silica gel; 10% methanol/chloroform) R$_f$=0.39.

Anal. calc'd. for C$_{44}$H$_{58}$N$_6$O$_7$·0.6 H$_2$: C, 66.58; H, 7.52; N, 10.59 Found: C, 66.56; H, 7.46; N, 10.38.

EXAMPLE 3

N$^2$-[N-[(1,1-Dimethylethoxy)carbonyl]-L-phenylalanyl]-N-[(S)-1-[1-hydroxy-2-[(1-oxo-3-phenylpropyl)amino]ethyl]-3-methylbutyl]-L-histidinamide A solution of the product of Example 2 (0.55 g., 0.70 mmole) in methanol (10 ml.) containing palladium on carbon catalyst (0.10 g.) is hydrogenated overnight. The reaction mixture is filtered and the filtrate is concentrated. The solid residue is triturated with ether to give 0.41 g. of N$^2$-[N-[(1,1-dimethylethoxy)carbonyl]-L-phenylalanyl]-N-[(S)-1-[1-hydroxy-2-[(1-oxo-3-phenylpropyl)amino]ethyl]-3-methylbutyl]-L-histidinamide as a white solid; m.p. (132°) 155°–160°. TLC (silica gel; 15% methanol/chloroform) R$_f$=0.55.

Anal. calc'd. for C$_{36}$H$_{50}$N$_6$O$_6$·0.2 H$_2$O: C, 64.88; H, 7.62; N, 12.61 Found: C, 64.88; H, 7.98; N, 12.40.

EXAMPLE 4

N$^2$-[N-[(1,1-Dimethylethoxy)carbonyl]-L-phenylalanyl]-1'-[(phenylmethoxy)methyl]-N-[(S)-1-[1-hydroxy-2-[1-oxo-2-[[(phenylmethyl)amino]carbonyl]-hexyl]amino]ethyl]-3-methylbutyl]-L-histidinamide (a) 2-[[(Phenylmethyl)amino]carbonyl]hexanoic acid N-Hydroxysuccinamide (1.72 g., 15 mmole) and dicyclohexylcarbodiimide (3.09 g., 15 mmole) are added to a solution of n-butylmalonic acid (2.4 g., 15 mmole) in dimethylformamide (35 ml.). After a few minutes a precipitate is observed. After 90 minutes, benzylamine (3.28 ml., 30 ml.) is added and the reaction mixture is stirred at room temperature overnight. The reaction is then diluted with saturated sodium bicarbonate (100 ml.), filtered, and the filtrate is washed with ethyl acetate (twice), and then acidified with 10% potassium bisulfate, saturated with sodium chloride and extracted with ethyl acetate (three times). The combined ethyl acetate extracts are washed with water (twice), dried over sodium sulfate, and concentrated into an oily residue (3.6 g.). Purification by flash chromatography (Whatman LPS-1 silica gel, eluting with 5% methanol/chloroform) and recrystallization from methanol/ether gives 0.55 g. of 2-[[(phenylmethyl)amino]carbonyl]hexanoic acid as a white solid; m.p. (95°) 100°–105°.

(b)
N-[(3S)-3-[[(1,1-Dimethylethoxy)carbonyl]amino]-2-hydroxy-5-methylhexyl]-2-[[(phenymethyl)amino]carbonyl]-pentanamide To a solution of (S)-[3-methyl-1-(3-amino-2-hydroxypropyl)butyl]carbamic acid, 1,1-dimethylethyl ester (0.32 g., 1.32 mmole) in tetrahydrofuran (25 ml., distilled) is added 2-[[(phenylmethyl)amino]carbonyl]hexanoic acid (0.33 g., 1.32 mmole), 1-hydroxybenzotriazole hydrate (0.20 g., 1.32 mmole) and dicyclohexylcarbodiimide (0.27 g., 1.32 mmole). After stirring overnight, the reaction mixture is filtered, the filtrate is concentrated, and the residue is redissolved in ethyl acetate (75 ml.). The ethyl acetate solution is washed with saturated sodium bicarbonate (three times), 10% potassium bisulfate (twice), and saturated sodium chloride, dried over sodium sulfate, and concentrated into a pale yellow foam (0.66 g.). Purification by flash chromatography (Whatman LPS-1 silica gel, eluting with ethyl acetate:hexane, 1:1) gives 0.29 g. of N-[(3S)-3-[[(1,1-dimethylethoxy)carbonyl]amino]-2-hydroxy-5-methylhexyl]-2-[[(phenylmethyl)amino]carbonyl]-pentanamide as a white solid; m.p. (91°) 107°–115°.

(c)
N-[(3S)-3-Amino-2-hydroxy-5-methylhexyl]-2-[[(phenylmethyl)amino]carbonyl]-pentanamide, monohydrochloride A solution of N-[(3S)-3-[[(1,1-dimethylethoxy)carbonyl]amino]-2-hydroxy-5-methylhexyl]-2-[[(phenylmethyl)amino]carbonyl]-pentanamide (0.7 g., 1.46 mmole) in saturated hydrochloric acid/ethyl acetate (25 ml.) is stirred at 0° for 2 hours. The reaction mixture is concentrated to a solid residue. Trituration with ether gives 0.60 g. of N-[(3S)-3-amino-2-hydroxy-5-methylhexyl]-2-[[(phenylmethyl)amino[carbonyl]-pentanamide, monohydrochloride as an oily white solid.

(d)
$N^2$-[N-[(1,1-Dimethylethoxy)carbonyl]-L-phenylalanyl]-1'-[(phenylmethoxy)methyl]-N-[(S)-1-[1-hydroxy-2-[[1-oxo-2-[[(phenylmethyl)amino]carbonyl]hexyl]amino]ethyl]-3-methylbutyl]-L-histidinamide To a cold (0°) solution of N-[(3S)-3-amino-2-hydroxy-5-methylhexyl]-2-[[(phenylmethyl)amino]carbonyl]-pentanamide, monohydrochloride (0.60 g., 1.45 mmole) in dimethylformamide (25 ml.) is added diisopropylethylamine (0.25 ml., 1.45 mmole), N-[N-[(1,1-dimethylethoxy)carbonyl-L-phenylalanyl]-1'-[(phenylmethoxy)methyl]-L-histidine (0.75 g., 1.45 mmole), 1-hydroxybenzotriazole hydrate (0.22 g., 1.45 mmole) and dicyclohexylcarbodiimide (0.30 g., 1.45 mmole). After stirring overnight (0°→room temperature), the reaction is diluted with ethyl acetate (150 ml.) and washed with water (twice), and saturated sodium bicarbonate (twice), dried over sodium sulfate, and concentrated. The residue (1.1 g., yellow foam) is purified by flash chromatography (Whatman LPS-1 silica gel, eluting with 5% methanol/chloroform) to give 0.81 g. of $N^2$-[N-[(1,1-dimethylethoxy)carbonyl]-L-phenylalanyl]-1'-[(phenylmethoxy)methyl]-N-[(S)-1-[1-hydroxy-2-[[1-oxo-2-[[(phenylmethyl)amino]carbonyl]hexyl]amino]ethyl]-3-methylbutyl]-L-histidinamide as an off-white foam; m.p. 112°–115°. TLC (silica gel; 10% methanol/chloroform) $R_f$=0.57.

Anal. calc'd. for $C_{49}H_{67}N_7O_8 \cdot 0.5$ $H_2O$: C, 66.04; H, 7.69; N, 11.00 Found: C, 66.10; H, 7.68; N, 10.58.

EXAMPLE 5
$N^2$-[N-[(1,1-Dimethylethoxy)carbonyl]-L-phenylalanyl]-N-[(S)-1-[1-hydroxy-2-[[1-oxo-2[[(phenylmethyl)amino]carbonyl]hexyl]amino]ethyl]-3-methylbutyl]-L-histidinamide, hydrochloride (1:1.25)

A solution of the product of Example 4 (0.176 g., 0.2 mmole) in methanol (50 ml.) containing 1N hydrochloric acid (0.2 ml., 0.2 mmole) and palladium hydroxide on carbon catalyst (0.05 g.) is hydrogenated overnight. The reaction mixture is filtered and the filtrate is concentrated. The solid residue is triturated with ether to give $N^2$-[N-[(1,1-dimethylethoxy)carbonyl]-L-phenylalanyl] -N-[(S)-1-[1-hydroxy-2-[[1-oxo-2-[[(phenyl (phenylmethyl)amino]carbonyl]hexyl]amino]ethyl]-3methylbutyl]-L-histidinamide, hydrochloride (1:1.25) as a white solid; m.p. (135°) 150°–155°. TLC (silica gel; 10% methanol/chloroform) $R_f$=0.39.

Anal. calc'd. for $C_{41}H_{59}N_7O_7 \cdot 1.25$ HCl·1.0 $H_2O$: C, 59.65; H, 7.60; N, 11.87; Cl, 5.36 Found: C, 59.60; H, 7.67; N, 11.61; Cl, 5.39.

EXAMPLE 6
$N^2$-[N-[(1,1-Dimethylethoxy)carbonyl]-L-phenylalanyl]-N-[(S)-1-[1-hydroxy-2-[(1-oxopentyl)-phentylamino]ethyl]-3-methylbutyl]-L-histidinamide

(a)
N-[(3S)-3-[[(1,1-Dimethylethoxy)carbonyl]-amino]-2-hydroxy-5-methylhexyl]-N-pentylpentanamide N-Amylamine (0.95 ml., 7.5 mmole) is added to a solution of (S)-[3-methyl-1-(2,3-epoxypropyl)butyl]carbamic acid, 1,1-dimethylethyl ester (1.75 g., 7.5 mmole) in methanol (100 ml.) and the reaction mixture is refluxed overnight. The reaction mixture is concentrated and the oil residue is dried in high vacuum for 2 hours. The residue is redissolved in tetrahydrofuran (50 ml., distilled) and valeryl chloride (0.97 ml., 8.25 mmole) and diisopropylethyl amine (1.44 ml., 8.25 mmole) are added. The reaction mixture is stirred at room temperature overnight, concentrated to ⅓ volume, diluted with ethyl acetate (100 ml.), washed with water (twice), saturated sodium bicarbonate (twice), and brine, dried over sodium sulfate, and concentrated into a pale yellow residue. Purification by flash chromatography (Whatman LPS-1 silica gel, eluting with 15% ethyl acetate/hexane) gives 1.4 g. of N-[(3S)-3-[[(1,1-dimethylethoxy)carbonyl]amino]-2-hydroxy-5-methylhexyl]-N-pentylpentanamide as a colorless oil.

(b)
N-[(3S)-3-Amino-2-hydroxy-5-methylhexyl]-N-pentylpentanamide

A solution of N-[(3S)-3-[[(1,1-dimethylethoxy)carbonyl]amino]-2-hydroxy-5-methylhexyl]-N-pentylpenide as a (1.4 g., 3.5 mmole) in saturated hydrochloric acid/ethyl acetate (100 ml.) is stirred at room temperature for 2.5 hours. The reaction mixture is concentrated to an oily residue. Trituration with hexane gives 1.16 g. of N-[(3S)-3-amino-2-hydroxy-5-methylhexyl]-N-pentylpentanamide as a yellow oily solid residue.

(c)

N²-[N-[(1,1-Dimethylethoxy)carbonyl]-L-phenylalanyl]-1'-[(phenylmethoxy)methyl]-N-[(S)-1-[1-hydroxy-2-[(1-oxopentyl)pentylamino]ethyl]-3-methylbutyl]-L-histidinamide To a cold (0°) solution of N-[(3S)-3-amino-2-hydroxy-5-methylhexyl]-N-pentylpentanamide (0.58 g., 1.72 mmole) in dimethylformamide (25 ml.) is added diisopropylethylamine (0.30 ml., 1.72 mmole), N-[N-[(1,1-dimethylethoxy)carbonyl]-L-phenylalanyl]-1'-[(phenylmethoxy)methyl]-L-histidine (0.89 g., 1.72 mmole), 1-hydroxybenzotriazole hydrate (0.26 g., 1.72 mmole), and dicyclohexylcarbodiimide (0.35 g., 1.72 mmole). After stirring overnight (0°→room temperature), the reaction mixture is diluted with ethyl acetate (100 ml.), washed with water (twice) and saturated sodium bicarbonate (twice), dried over sodium sulfate, and concentrated to give 1.2 g. of white solid product. Purification by flash chromatography (Whatman LPS-1 silica gel, eluting with 5% methanol/chloroform) and recrystallization from warm ether gives 0.53 g. of N²-[N-[(1,1-dimethylethoxy)carbonyl]-L-phenylalanyl]-1'-[(phenylmethoxy)methyl]-N-[(S)-1-[1-hydroxy-2-[(1-oxopentyl)pentylamino]ethyl]-3-methylbutyl]-L-histidinamide as a white solid; m.p. (130°) 155°-160°.

(d)

N²-[N-[(1,1-Dimethylethoxy)carbonyl]-L-phenylalanyl]-N-[(S)-1-[1-hydroxy-2-[(1-oxop ethyl]-3-methylbutyl]-L-histidinamide A solution of the product from part (c) (0.95 g., 1.18 mmole) in methanol (60 ml.) containing palladium hydroxide on carbon catalyst (200 mg.) is hydrogenated overnight. The reaction mixture is filtered and the filtrate is concentrated. The solid residue is triturated with ether to give 0.62 g. of N²-[N-[(1,1-dimethylethoxy)carbonyl]-L-phenylalanyl]-N-[(S)-1-[1-hydroxy-2-[(1-oxopentyl)pentylamino]ethyl]-3-methylbutyl]-L-histidinamide as a white solid; m.p. (96°) 105°-110°. TLC (silica gel; 10% methanol/chloroform) $R_f$=0.57.

Anal. calc'd. for $C_{37}H_{60}N_6O_6 \cdot 1.9 H_2O$: C, 61.79; H, 8.94; N, 11.68 Found: C, 61.79; H, 8.73; N, 11.53.

EXAMPLE 7

N²-[N-[(1,1-Dimethylethoxy)carbonyl]-L-phenylalanyl]-N-[(S)-1-[1-hydroxy-2-[(1-oxo-3phrnylpropyl)pentylamino]ethyl]-3-methylbutyl]-L-histidinamide (a)

N-[(3S)-3-[[(1,1-Dimethylethoxy)carbonyl]amino]-2-hydroxy-5-methylhexyl]-N-(pentyl)phenylpropylamide N-Amylamine (0.95 ml., 7.5 mmole) is added to a solution of (S)-[3-methyl-1-(2,3-epoxypropyl)butyl]carbamic acid, 1,1-dimethylethyl ester (1.75 g., 7.5 mmole) in methanol (100 ml.). The reaction mixture is concentrated and the oily residue obtained is dried in high vacuum for one hour.

Hydrocinnamic acid (1.24 g., 8.25 mmole) is dissolved in ether (25 ml.) and oxalyl chloride (0.72 ml., 8.25 mmole) and a few drops of dimethylformamide are added. After 45 minutes the reaction mixture is concentrated and dried in high vacuum for one hour to give the acid chloride of hydrocinnamic acid.

The obtained acid chloride is dissolved in tetrahydrofuran (25 ml.) and added to the above obtained oily residue of amine along with diisopropylethylamine (1.44 ml., 8.25 mmole). The reaction mixture is stirred at room temperature under nitrogen overnight. The reaction mixture is diluted with ethyl acetate (150 ml.), washed with saturated sodium bicarbonate (twice), 10% potassium bisulfate (twice), and water (twice), dried over sodium sulfate, and concentrated to give 2.8 g. of pale yellow oily residue. Purification by flash chromatography (Whatman LPS-1 silica gel; eluting with ethyl acetate/hexane, 1:1) gives 1.9 g. of N-[(3S)-3-[[(1,1-dimethyl-ethoxy)carbonyl]amino]-2-hydroxy-5-methylhexyl[-N-(pentyl)phenylpropylamide as a colorless oil.

(b)

N-[(3S)-3-Amino-2-hydroxy-5-methylhexyl]-N-(pentyl)phenylpropylamide

A solution of N-[(3S)3-[[(1,1-dimethylethoxy)carbonyl]amino]-2-hydroxy-5-methylhexyl]-N-(pentyl)p (1.90 g., 4.23 mmole) in saturated hydrochloric acid-/ethyl acetate (25 ml.) is stirred at 0° for 2 hours. The reaction mixture is concentrated to a solid residue. Trituration with ether gives 1.58 g. of N-[(3S)-3-amino-2-hydroxy-5-methylhexyl-N-(pentyl)phenylpropylamide as a hygroscopic white solid.

(c)

N²[-N-[(1,1-Dimethylethoxy)carbonyl]-L-phenylalanyl]-1'-[(phenylmethoxy)methyl]-N-[(S)-1-[1-hydroxy-2-[(1-oxo-3-phenylpropyl)pentylamino]ethyl]-3-methylbutyl]-L-histidinamide To a cold (0°) solution of N-[(3S)-3-amino-2-hydroxy-5-methylhexyl-N-(pentyl)phenylpropylamide (1.58 g., 4.25 mmole) in dimethylformamide (25 ml.) is added diisopropylethylamine (0.73 ml., 4.23 mmole), N-[N-[N-[(1,1-dimethylethoxy)carbonyl]-L-phenylalanyl]-1'-[(phenylmethoxy)methyl]-L-histidine (2.21 g., 4.23 mmole), 1-hydroxybenzotriazole hydrate (0.64 g., 4.23 mmole) and dicyclohexylcarbodiimide (0.87 g., 4.23 mmole). After stirring overnight (0°→room temperature), the reaction mixture is diluted with ethyl acetate (200 ml.), washed with water (twice) and saturated sodium bicarbonate (twice), dried over sodium sulfate, and concentrated into an oily solid. Purification by flash chromatography (Whatman LPS-1 silica gel, eluting with 10% methanol/chloroform) gives 1.52 g. of N²-[N-[(1,1-dimethylethoxy)carbonyl]-L-phenylalanyl]-1'-[(phenylmethoxy)methyl]-N-[(S)-1-[1-hydroxy-2-[(1-oxo-3-phenylpropyl)pentylamino]ethyl]-3-methylbutyl]-L-histidinamide as an off-white foam.

(d)

N²-[N-[(1,1-Dimethylethoxy)carbonyl]-L-phenylalanyl]-N-[(S)-1-[1-hydroxy-2-[(1-oxo-3-phenylpropyl)pentylamino]ethyl]-3-methylbutyl]-L-histidinamide A solution of the product from part (c) (0.80 g., 0.95 mmole) in methanol (50 ml.) containing palladium on carbon catalyst (200 mg.) is hydrogenated overnight. The reaction mixture is filtered and the filtrate is concentrated. The solid residue is triturated with ether to give 0.61 g. of product. Purification by flash chromatography (Whatman LPS-1 silica gel, eluting with 2% methanol/chloroform, 4% methanol/chloroform) gives 0.30 g. of N²-[N-[(1,1-dimethylethoxy)carbonyl]-L-phenylalanyl]-N-[(S)-1-[1-hydroxy-2-[(1-oxo-3-phenylpropyl)pentylamino]ethyl]-3-methylbutyl]-L-histidinamide; m.p. (175°) 196°-199°. TLC (silica gel; 10% methanol/chloroform) $R_f$=0.55.

Anal. calc'd. for $C_{41}H_{59}N_6O_6 \cdot 0.5\ H_2O$: C, 66.45; H, 8.16; N, 11.34 Found: C, 66.59; H, 8.24; N, 11.59.

EXAMPLE 8

$N^2$-[N-[(1,1-Dimethylethoxy)carbonyl]-L-phenylalanyl]-N-[(S)-1-[1-hydroxy-2-[(1-oxopentyl)-(phenylmethyl)amino]ethyl]-3-methylbutyl]-L-histidinamide

(a)
N-[(3S)-3-[[(1,1-Dimethylethoxy)carbonyl]amino]-2-hydroxy-5-methylhexyl]-N-(phenylmethyl)pentanamide Benzylamine (1.02 ml., 9.4 mmole) is added to a solution of (S)-[3-methyl-1-(2,3-epoxypropyl)butyl]carbamic acid, 1,1-dimethylethyl ester (2.2 g., 9.4 mmole) in methanol (60 ml.). The mixture is refluxed overnight, concentrated on a rotary evaporator, and the residue is dried for 2 hours in high vacuum. The oily residue is redissolved in tetradydrofuran (50 ml., distilled) and valeryl chloride (1.23 ml., 10.34 mmole) and diisopropylethylamine (1.80 ml., 10.34 mmole) are added. After stirring overnight at room temperature, the reaction mixture is concentrated to ⅓ volume, diluted with ethyl acetate (100 ml.), washed with saturated sodium bicarbonate (twice) and water (twice), dried over sodium sulfate, and concentrated to a yellow oil (4.0 g.). Purification by flash chromatography (Whatman LPS-1 silica gel; eluting with 10% ethyl acetate/hexane and 25% ethyl acetate/hexane) gives 3.2 g. of N-[(3S)-3-[[(1,1-dimethylethoxy)carbonyl]amino]-2-hydroxy-5-methylhexyl]-N-(phenylmethyl)pentanamide as a pale yellow oil.

(b)
N-[(3S)-3-Amino-2-hydroxy-5-methylhexyl]-N-(phenylmethyl)pentanamide

A solution of N-[(3S)-3-[[(1,1-dimethylethoxy)carbonyl]amino]-2-hydroxy-5-methyl-hexyl]-N-(phenylmethyl)pentanamide (3.2 g., 7.6 mmole) in saturated hydrochloric acid/ethyl acetate (50 ml.) is stirred at 0° for 2 hours. The reaction mixture is concentrated to an oily residue. Trituration with ether gives 2.71 g. of N-[(3S)-3-amino-2-hydroxy-5-methylhexyl]-N-(phenylmethyl)pentanamide as a white foam.

(c)
$N^2$-[N-[(1,1-Dimethylethoxy)carbonyl]-L-phenylalanyl]-1'-[(phenylmethoxy)methyl]-N-[(S)-1-[1-hydroxy-2-[(1-oxopentyl)(phenylmethyl)amino]ethyl]-3-methylbutyl]-L-histidinamide To a cold (0°) solution of N-[(3S)-3-amino-2-hydroxy-5-methylhexyl-N-(phenylmethyl)pentanamide (2.71 g., 7.6 mmole) in dimethylformamide (1.31 ml., 7.6 mmole) is added diisopropylethylamine (1.31 ml., 7.6 mmole), N-[N-[(1,1-dimethylethoxy)carbonyl]-L-phenylalanyl]-1'-[(phenylmethoxy)methyl]-L-histidine (3.98 g., 7.6 mmole), 1-hydroxybenzotriazole hydrate (1.16 g., 7.6 mmole) and dicyclohexylcarbodiimide (4.56 g., 7.6 mmole). After stirring overnight (0°→room temperature), the reaction mixture is diluted with ethyl acetate (500 ml.), washed with water (twice) and saturated sodium bicarbonate (twice), dried over sodium sulfate, and concentrated to give 5.1 g. of product as a yellow foam. Purification by flash chromatography (Whatman LPS-1 silica gel, eluting with 3% methanol/-chloroform) gives 3.36 g. of $N^2$-[N-[(1,1-dimethylethoxy)carbonyl]-L-phenyl-alanyl]-1'-[(phenylmethoxy)methyl]-N[(S)-1-[1-hydroxy-2-[(1-oxopentyl)(phenylmethyl)amino]ethyl]-3-methylbutyl]-L-histidinamide as a white foam.

(d)
$N^2$-[N-[(1,1-Dimethylethoxy)carbonyl]-L-phenylalanyl]-N-[(S)-1-[1-hydroxy-2-[(1-oxopentyl)(-phenylmethyl)amino]ethyl]-3-methylbutyl]-L-histidinamide A solution of the product from part (c) (1.0 g, 1.21 mmole) in methanol (100 ml.) containing palladium hydroxide on carbon catalyst (200 mg.) is hydrogenated overnight. The reaction mixture is filtered and the filtrate is concentrated. The solid residue is triturated with ether to give 1.0 g. of product as a white solid. Purification by flash chromatography (Whatman LPS-1 silica gel, eluting with 2.5% methanol/chloroform, 5.0% methanol/chloroform) gives 0.29 g. of $N^2$-[N-[(1,1-dimethylethoxy)carbonyl]-L-phenylalanyl]-N-[(S)-1-[1-hydroxy-2-[(1-oxopentyl)(phenylmethyl)amino]ethyl]-3-methylbutyl]-L-histidinamide; m.p. (93°) 106°–108°. TLC (silica gel; 10% methanol/chloroform) $R_f$=0.37.

Anal. calc'd for $C_{39}H_{56}N_6O_6 \cdot 0.5\ H_2O$: C, 65.70; H, 7.98; N, 11.79 Found: C, 65.73; H, 7.96; N, 11.72.

EXAMPLE 9

N-[(1S)-1-(Cyclohexylmethyl)-2-hydroxy-3-[[1-oxo-2-[[(phenylmethyl)amino]carbonyl]hexyl]amino]propyl]-$N^2$-N-[(1,1-dimethylethoxy)carbonyl]-L-phenylalanyl]-L-histidinamide

(a)
(1S)-[3-Chloro-1-(phenylmethyl)-2-hydroxypropyl]carbamic acid, 1,1-dimethylethyl ester Sodium borohydride (10.4 g., 275 mmole) is added with stirring to a solution of (S)-[3-chloro-1-(phenylmethyl)-2-oxopropyl]carbamic acid, 1,1-dimethylethyl ester (29.2 g., 110 mmole) in tetrahydrofuran/water (100 ml./20 ml.) at 0°. After two hours, the reaction mixture is quenched with 10% potassium bisulfate, diluted with ethyl acetate (300 ml.), washed with water (twice), saturated sodium bicarbonate (twice), and 10% potassium bisulfate (twice), dried over sodium sulfate, and concentrated to give 21.1 g. of (1S)-[3-chloro-1-(phenylmethyl)-2-hydroxypropyl]carbamic acid, 1,1-dimethylethyl ester as a white solid.

(b) (S)-[1-(2,3-Epoxypropyl)phenylmethyl]carbamic acid, 1,1 dimethylethyl ester Sodium hydride (5.63 g., 140.76 mmole) is added to a solution of (1S)-[3-chloro-1-(phenylmethyl)-2-hydroxypropyl]carbamic acid, 1,1-dimethylethyl ester (21.1 g., 70.38 mmole) in tetrahydrofuran (150 ml., distilled) and the reaction mixture is stirred overnight. It is then filtered and the filtrate is concentrated. The oily residue is redissolved in ethyl acetate (500 ml.), washed with water (twice), saturated sodium bicarbonate (twice), and 10% potassium bisulfate (twice), dried over sodium sulfate, and concentrated into a white solid residue (16.0 g.). Purification by flash chromatography (Whatman LPS-1 silica gel, eluting with 25% ethyl acetate/hexane) gives 12.6 g. of (S)-[1-(2,3-epoxypropyl)phenylmethyl]carbamic acid, 1,1-dimethylethyl ester as a white solid.

(c)
(1S)-[1-(3-Amino-2-hydroxypropyl)phenylmethyl]carbamic acid, 1,1-dimethylethyl ester (S)-[1-(2,3-Epoxypropyl)phenylmethyl]carbamic acid, 1,1-dimethylethyl ester (6.5 g., 24.68 mmole) is added to a solution of saturated ammonia/methanol (250 ml.) and stirred for 36 hours at room temperature. The reaction mixture is concentrated to give 6.8 g. of (1S)-[1-(3-amino-2-hydroxypropyl)phenylmethyl]carbamic acid, 1,1-dimethylethyl ester as a solid residue.

(d)
(1S)[1-(3-Amino-2-hydroxypropyl)(cyclohexylmethyl)-]carbamic acid, 1,1-dimethylethyl ester, monohydrochloride Platinum (IV) oxide (200 mg.) is added to a solution of (1S)-[1-(3-amino-2-hydroxypropyl)phenylmethyl]-carbamic acid, 1,1-dimethylethyl ester (0.98 g., 3.5 mmole) in absolute ethanol (50 ml.) containing 1N hydrochloric acid (3.5 ml., 3.5 mmole) and hydrogenated at 55 psi overnight. The reaction mixture is filtered and the oily residue is triturated with hexane to give 1.07 g. of (1S)[1-(3-amino-2-hydroxypropyl)(cyclohexylmethyl)]carbamic acid, 1,1-dimethylethyl ester, monohydrochloride as a white solid; m.p. 58°–60°.

(e)
N-[(3S)-3-[[(1,1-Dimethylethoxy)carbonyl]-amino]-2-hydroxy-4-(cyclohexyl)butyl]-2-[[methyl)amino]carbonyl]-pentanamide.

N-Hydroxysuccinimide (17.2 g., 150 mmole) is added to a solution of n-butylmalonic acid (24.0 g., 150 mmole) in dimethylformamide (100 ml.). After stirring at room temperature for one hour, benzylamine (32.8 ml., 300 mmole) is added to the suspension and the mixture is stirred overnight. The reaction mixture is poured into 2N sodium hydroxide (500 ml.) and filtered. The filtrate is washed with ethyl acetate (2×500 ml.), and the aqueous portion is acidified with 2N hydrochloric acid. The precipitated solids are filtered to give 12.3 g. of 2-[(phenylmethyl)amino]carbonyl]hexanoic acid; m.p. (95° ).

To a solution of (1S)-[1-(3-amino-2-hydroxy-propyl)-(cyclohexylmethyl)]carbamic acid, 1,1-dimethylethyl ester, monohydrochloride (1.0 g., 3.10 mmole) in tetrahydrofuran (50 ml., distilled) is added diisopropylethylamine (0.54 ml., 3.10 mmole), 2-[[(phenylmethyl-)amino]carbonyl]hexanoic acid (0.77 g., 3.10 mmole), 1-hydroxybenzotriazole hydrate (0.47 g., 3.10 mmole) and dicyclohexylcarbodiimide (0.64 g., 3.10 mmole). After stirring overnight, the reaction mixture is filtered and the filtrate is concentrated. The residue is redissolved in ethyl acetate (200 ml.), washed with saturated sodium bicarbonate (twice), 10% potassium bisulfate (twice), and saturated sodium chloride, dried over sodium sulfate, and concentrated into a white solid (1.6 g.). Purification by flash chromatography (Whatman LPS-1 silica gel, eluting with 2% methanol/ chloroform) gives 1.1 g. of N-[(3S)-3-[[(1,1-dimethylethoxy)carbonyl]amino]-2-hydroxy-4-(cyclohexyl)butyl]-2-[[(phenylmethyl)amino]-carbonyl]-pentanamide as a white solid; m.p. (75° ) 87°–118°.

(f)
N-[(3S)-3-Amino-2-hydroxy-4-(cyclohexyl)butyl]-2-[[(phenylmethyl)amino]carbonyl]pentanamide, monohydrochloride A solution of the product from part (e) (1.1 g., 2.1 mmole) in saturated hydrochloric acid/ethyl acetate (50 ml.) is stirred at 0° for 2 hours. The reaction mixture is concentrated to a solid residue. Trituration with ether gives 0.97 g. of N-[(3S)-3-amino-2-hydroxy-4-(cyclohexyl)butyl]-2-[[(phenymethyl)amino]carbonyl]-pentanamide, monohydrochloride as a white solid.

(g)
N-[(1S)-1-(Cyclohexylmethyl)-2-hydroxy-3-[[1-oxo-2-[[(phenylmethyl)amino]carbonyl]hexyl]-amino]propyl]-$N^2$-[N-[(1,1-dimethylethoxy)carbonyl]-L-phenylalanyl]-1′-[(phenylmethoxy)methyl]-L-histidinamide To a cold (0° ) solution of N-[(3S)-3-amino-2-hydroxy-4-(cyclohexyl)butyl]-2-[(phenylmethyl)-amino]carbonyl]-pentanamide, monohydrochloride (0.97 g., 2.1 mmole) in dimethylformamide (25 ml.) is added diisopropylethylamine (0.36 ml., 2.1 mmole), N-[N-[(1,1-dimethylethoxy)carbonyl]-L-phenylalanyl]-1′-[(phenylmethoxy)methyl]-L-histidine (1.09 g., 2.1 mmole), 1-hydroxybenzotriazole hydrate (0.32 g., 2.1 mmole), and dicyclohexylcarbodiimide (0.43 g., 2.1 mmole). After stirring overnight (0°→room temperature), the reaction mixutre is diluted with ethyl acetate (200 ml.), washed with water (twice) and saturated sodium bicarbonate (twice), dried over sodium sulfate, and concentrated to an oily solid (2.5 g.). Purification by flash chromatography (Whatman LPS-1 silica gel; eluting with 10% methanol/chloroform) gives 1.61 g. of N-[(1S)-1-(cyclohexylmethyl)-2-hydroxy-3-[[1-oxo-2-[[(phenylmethyl)amino]carbonyl]hexyl]amino]propyl-$N^2$-[N-[(1,1-dimethylethoxy)carbonyl-L-phenylalanyl]-1′-[(phenylmethoxy)methyl]-L-histidinamide as a white solid, m.p. (65° ) 110°–117°.

(h)
N-[(1S)-1-(Cyclohexylmethyl)-2-hydroxy-3-[[(1-oxo-2-[[(phenylmethyl)amino]carbonyl]hexyl]-amino]propyl]-$N^2$-[N-[(1,1-dimethylethoxy)carbonyl]-L-phenylalanyl]-L-histidinamide.

A solution of the product from part (g) (1.60 g., 1.74 mmole) in methanol (50 ml.) containing palladium hydroxide on carbon catalyst (250 mg.) is hydrogenated overnight. The reaction mixture is filtered and the filtrate is concentrated. The solid residue is triturated with ether to give 1.55 g. of crude product. Purification by flash chromatography (Whatman LPS-1 silica gel, eluting with 2% methanol/chloroform→5% methanol/-chloroform) gives 0.22 g. of N-[(1S)-1-(cyclohexylmethyl)-2-hydroxy-3-[[(1-oxo-2-[[(phenylmethyl)amino]-carbonyl]hexyl]-amino ]propyl-$N^2$-[N-[(1,1-dimethylethoxy)carbonyl]-L-phenylalanyl]-L-histidinamide; m.p. (105° ) 110°–115°. TLC (silica gel; 10% methanol/-chloroform) $R_f$=0.34.

Anal. calc'd. for: $C_{44}H_{63}N_7O_7 \cdot 1.5\ H_2O$; C,63.74; H,8.02; N,11.82 Found: C,63.73; H,7.85; N,11.57.

EXAMPLES 10–36

Following the procedure of Examples 1 to 9, additional compounds within the scope of this invention can be prepared having the formula $$X-NH-\underset{R_4}{\underset{|}{CH}}-\overset{O}{\overset{\|}{C}}-NH-\underset{R_3}{\underset{|}{CH}}-\underset{OH}{\underset{|}{CH}}-CH_2-\underset{R_2}{\underset{|}{N}}-\overset{O}{\overset{\|}{C}}-\underset{R_1}{\underset{|}{CH}}-R_9.$$

| Example | X | R4 | R3 | R2 | R1 | R9 |
|---|---|---|---|---|---|---|
| 10 | (H3C)3C—O—C(=O)—NH—CH(CH2-Ph)—C(=O)— | —CH2-(imidazole) | —CH2CH(CH3)2 | —H | —H | —CH2-(pyridine) |
| 11 | Ph-CH2-O—C(=O)—NH—CH(CH2-Ph)—C(=O)— | —CH2-(imidazole) | —CH2CH(CH3)2 | —H | —H | —CH2-(cyclohexyl) |
| 12 | (H3C)3C—O—C(=O)—NH—CH(CH2-imidazole)—C(=O)— | —CH2-Ph | —CH2CH(CH3)2 | —H | —H | -(p-OCH3-C6H4) |
| 13 | (H3C)3C—O—C(=O)—NH—CH((CH2)2-Ph)—C(=O)— | —CH2-(indole) | —CH2CH(CH3)2 | —CH2-Ph | —H | —(CH2)2-Ph |

-continued $$X-NH-\overset{R_4}{\underset{}{CH}}-\overset{O}{\underset{}{C}}-NH-\overset{R_3}{\underset{}{CH}}-CH-CH_2-N-\overset{R_2}{\underset{}{C}}-\overset{O}{\underset{}{C}}-\overset{R_1}{\underset{}{CH}}-R_9.$$
$$\phantom{X-NH-CH-C-NH-CH-}\overset{}{\underset{OH}{|}}$$

| Example | X | R4 | R3 | R2 | R1 | R9 |
|---|---|---|---|---|---|---|
| 14 | (H3C)3C—O—C(=O)—NH—CH(CH2-phenyl)—C(=O)— | —CH2-(2-pyridyl) | —CH2-cyclohexyl | —H | —H | —(CH2)2—CH3 |
| 15 | (H3C)3C—O—C(=O)—NH—CH(CH2-naphthyl)—C(=O)— | —CH2-(imidazolyl) | —CH2-cyclohexyl | —H | —(CH2)3—CH3 | —C(=O)—NH—CH2-phenyl |
| 16 | phenyl-CH2—O—C(=O)—NH—CH(CH2-(4-pyridyl))—C(=O)— | —CH2-phenyl | —CH2CH(CH3)2 | —CH2-phenyl | —H | —CH3 |
| 17 | (HC3)3C—O—C(=O)—NH—CH(CH2-phenyl)—C(=O)— | —CH2-(imidazolyl) | —CH2-(2-pyridyl) | —(CH2)4—CH3 | —H | —C(=O)—NH2 |

-continued $$X-NH-\overset{\overset{R_4}{|}}{C}H-\overset{\overset{O}{\|}}{C}-NH-\overset{\overset{R_3}{|}}{C}H-\overset{}{C}H-CH_2-\overset{\overset{R_2}{|}}{N}-\overset{\overset{O}{\|}}{C}-\overset{\overset{R_1}{|}}{C}H-R_9.$$
$$\phantom{XXXXXXXXXXXXXXXXXXX}\overset{|}{OH}$$

| Example | X | R4 | R3 | R2 | R1 | R9 |
|---|---|---|---|---|---|---|
| 18 | PhCH₂-C(=O)-NH-CH(CH₂Ph)-C(=O)- | -CH₂-(imidazole) | -CH₂-cyclohexyl | -(CH₂)₂CH₃ | -H | -C(=O)-NH-C₂H₅ |
| 19 | CH₂Ph-SO₂-NH-CH(CH₂Ph)-C(=O)- | -CH₂-(imidazole) | -CH₂CH(CH₃)₂ | -H | -H | -CH₂-(2-thienyl) |
| 20 | (furan-2-yl)CH₂-O-C(=O)-NH-CH(CH₂Ph)-C(=O)- | -CH₂-(imidazole) | -CH₂CH(CH₃)₂ | -CH₂-Ph | -H | -(CH₂)₂-CH₃ |
| 21 | PhCH₂-O-C(=O)-NH-CH(CH₂Ph)-C(=O)- | -CH₂-(imidazole) | -CH₂-cyclohexyl | -H | -H | -CH₂-Ph |

-continued $$X-NH-\overset{R_4}{\underset{}{CH}}-\overset{O}{\underset{}{C}}-NH-\overset{R_3}{\underset{}{CH}}-\overset{R_2}{\underset{}{CH}}-\overset{}{\underset{OH}{CH}}-CH_2-\overset{O}{\underset{}{N}}-\overset{R_1}{\underset{}{CH}}-R_9.$$

| Example | X | R4 | R3 | R2 | R1 | R9 |
|---|---|---|---|---|---|---|
| 22 | (H3C)2CHCH2—O—C(=O)—NH—CH(CH2Ph)—C(=O)— | —CH2-(imidazole) | —CH2CH(CH3)2 | —H | —(CH2)3—CH3 | —C(=O)—NH—CH2—Ph |
| 23 | Ph-SO2—NH—CH(CH2Ph)—C(=O)— | —CH2-(imidazole) | —CH2—Ph | —H | —(CH2)3—CH3 | —C(=O)—NH—CH2-cyclohexyl |
| 24 | (H3C)2CHCH2—SO2—NH—CH(CH2Ph)—C(=O)— | —CH2-(imidazole) | —CH2CH(CH3)2 | —H | —(CH2)3—CH3 | —C(=O)—NH—(CH2)2—Ph |
| 25 | (H3C)3C—O—C(=O)—NH—CH(CH2Ph)—C(=O)— | —CH2-(imidazole) | —CH2CH(CH3)2 | —H | —H | —C(=O)—OH |

-continued $$X-NH-CH(R_4)-\overset{O}{\underset{\|}{C}}-NH-CH(R_3)-\underset{\underset{OH}{|}}{CH}-CH_2-N(R_2)-\overset{O}{\underset{\|}{C}}-CH(R_1)-R_9$$

| Example | X | R₄ | R₃ | R₂ | R₁ | R₉ |
|---|---|---|---|---|---|---|
| 26 | (H₃C)₃C—O—C(=O)—NH—CH(CH₂Ph)—C(=O)— | —CH₂-(imidazolyl) | —CH₂CH(CH₃)₂ | —H | —H | —C(=O)—NH—CH₂—C(=O)—OH |
| 27 | (H₃C)₃C—O—C(=O)— | —CH₂-(imidazolyl) | —CH₂CH(CH₃)₂ | —(CH₂)₄—CH₃ | —H | —(CH₂)₂—CH₃ |
| 28 | PhCH₂—O—C(=O)— | —CH₂-(imidazolyl) | —CH₂-(cyclohexyl) | —(CH₂)₄—CH₃ | —H | —CH₂—Ph |
| 29 | (H₃C)₃C—O—C(=O)— | —CH₂-(imidazolyl) | —CH₂CH(CH₃)₂ | —H | —(CH₂)₃—CH₃ | —C(=O)—NH—CH₂—Ph |
| 30 | PhCH₂—O—C(=O)— | —CH₂—Ph | —CH₂-(imidazolyl) | —H | —H | —(CH₂)₃—CH₃ |
| 31 | (H₃C)₂CHCH₂—O—C(=O)— | —CH₂-(indol-3-yl) | —CH₂—Ph | —CH₂—Ph | —H | —C(=O)—NH—C₂H₅ |

-continued $$X-NH-\underset{R_4}{\underset{|}{CH}}-\overset{O}{\overset{\|}{C}}-NH-\underset{R_3}{\underset{|}{CH}}-\underset{OH}{\underset{|}{CH}}-CH_2-\underset{R_2}{\underset{|}{N}}-\overset{O}{\overset{\|}{C}}-\underset{R_1}{\underset{|}{CH}}-R_9$$

| Example | X | R$_4$ | R$_3$ | R$_2$ | R$_1$ | R$_9$ |
|---|---|---|---|---|---|---|
| 32 | C$_6$H$_5$—SO$_2$— | —CH$_2$-(imidazole) | —CH$_2$CH(CH$_3$)$_2$ | —H | —H | —C(O)—OCH$_3$ |
| 33 | C$_{10}$H$_7$—CH$_2$—CH(CH$_2$C$_6$H$_5$)—C(O)— | —CH$_2$-(imidazole) | —CH$_2$-cyclohexyl | —H | —(CH$_2$)$_3$—CH$_3$ | —CH$_2$—C$_6$H$_5$ |
| 34 | C$_6$H$_5$—CH(CH$_2$-naphthyl)—C(O)— | —CH$_2$-(imidazole) | —CH$_2$-cyclohexyl | —H | —(CH$_2$)$_3$—CH$_3$ | —C(O)—NH—CH$_2$—C$_6$H$_5$ |
| 35 | (H$_3$C)$_3$C—O—C(O)—NH—CH(CH$_2$C$_6$H$_5$)—C(O)— | —CH$_2$-(imidazole) | —CH$_2$CH(CH$_3$)$_2$ | —H | —H | —C(O)—NH—CH(CH$_2$C$_6$H$_5$)—C(O)—OH |
| 36 | (H$_3$C)$_3$C—O—C(O)— | —CH$_2$-(imidazole) | —CH$_2$CH(CH$_3$)$_2$ | —H | —H | —C(O)—NH—CH(CH$_2$C$_6$H$_5$)—C(O)—O—C(CH$_3$)$_3$ |

EXAMPLE 37

1000 tablets each containing the following ingredients:

| | |
|---|---|
| N—[(1S)-1-(Cyclohexylmethyl)-2-hydroxy-3-[[1-oxo-2-[[(phenylmethyl)amino]carbonyl]hexyl]-amino]propyl]-N²-[N—[(1,1-dimethylethoxy)carbonyl]-L-phenylalanyl]-L-histidinamide | 250 mg. |
| Cornstarch | 100 mg. |
| Gelatin | 20 mg. |
| Avicel (microcrystalline cellulose) | 50 |
| Magnesium stearate | 5 mg. |
| | 425 mg. | are prepared from sufficient bulk quantities by mixing the N-[(1S)-1-(cyclohexylmethyl)-2-hydroxy-3-[[1-oxo-2-[[(phenylmethyl)amino]carbonyl]hexyl]-amino ]propyl]-N²-[N—[(1,1-dimethylethoxy)carbonyl]-L-phenylalanyl]-L-histidinamide and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 250 mg. of active ingredient.

In a similar manner, tablets containing 250 mg. of the product of any of Examples 1 to 8 and 10 to 36 can be prepared.

A similar procedure can be employed to form tablets containing 500 mg. of active ingredient.

EXAMPLE 38

An injectable solution is prepared as follows:

| | |
|---|---|
| N²—[N—[(1,1-Dimethylethoxy)-carbonyl]-L-phenylalanyl]-N—[(S)-1-[1-hydroxy-2-[(1-oxopentyl)(phenylmethyl)amino]-ethyl]-3-methylbutyl]-L-histidinamide | 1000 g. |
| Methyl paraben | 5 g. |
| Propyl paraben | 1 g. |
| Sodium chloride | 5 g. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 200 mg. of active ingredient per ml. of solution for injection.

In a similar manner, an injectable solution containing 200 mg. of active ingredient per ml. of solution can be prepared for the product of any of Examples 1 to 7 and 9 to 36.

EXAMPLE 39

1000 tablets each containing the following ingredients:

| | |
|---|---|
| N—[(1S)-1-(Cyclohexylmethyl)-2-hydroxy-3-[[1-oxo-2-[[(phenylmethyl)amino]carbonyl]hexyl]-amino]propyl]-N²—[N—[(1,1- | 500 mg. |
| dimethylethoxy)carbonyl]-L-phenylalanyl]-L-histidinamide | |
| Avicel | 300 mg. |
| Lactose | 113 mg. |
| Cornstarch | 15.5 mg. |
| Hydrochlorothiazide | 14.5 mg. |
| Stearic acid | 7 mg. |
| | 950 mg. | are prepared from sufficient bulk quantities by slugging the N-[(1S)-1-(cyclohexylmethyl)-2-hydroxy-3-[[1-oxo-2-[[(phenylmethyl)amino]carbonyl]hexyl]amino]-propyl]-N²-[N-[(1,1-dimethylethoxy)carbonyl]-L-phenylalanyl]-L-histidinamide, Avicel, and a portion of the stearic acid. The slugs are ground and passed through a #2 screen, then mixed with the hydrochlorothiazide, lactose, cornstarch, and remainder of the stearic acid. The mixture is compressed into 950 mg. capsule shaped tablets in a tablet press.

In a similar manner, tablets can be prepared containing 500 mg. of the product of any of Examples 1 to 8 and 10 to 36.

What is claimed is:

1. A compound of the formula

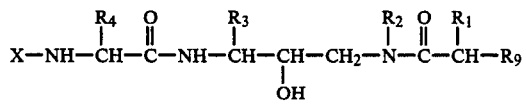

including a pharmaceutically acceptable salt thereof wherein:

X is

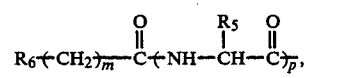

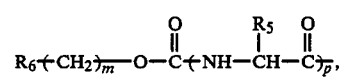

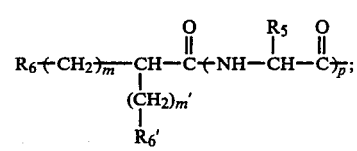

p is zero or one;

$R_3$, $R_4$, $R_5$, $R_{11}$, and $R_{12}$ are independently selected from the group consisting of hydrogen, lower alkyl, halo substituted lower alkyl, —$(CH_2)_n$-aryl, —$(CH_2)_n$-heterocyclo, —$(CH_2)_n$—OH, —$(CH_2)_n$-$NH_2$, —$(CH_2)_n$—SH, —$(CH_2)_n$—S-lower alkyl, —$(CH_2)_n$—O—$(CH_2)_g$—OH, —$(CH_2)_n$—O—$(CH_2)_g$—$NH_2$, —$(CH_2)_n$—S—$(CH_2)_g$—OH, —$(CH_2)_n$—S—$(CH_2)_g$—OH,

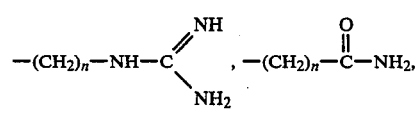

-continued

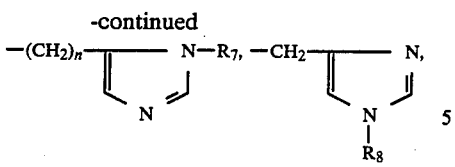

and —(CH$_2$)$_n$-cycloalkyl;

R$_1$ and R$_2$ are independently selected from the group consisting of hydrogen, lower alkyl, —(CH$_2$)$_m$-aryl, —(CH$_2$)$_m$-cycloalkyl and —(CH$_2$)$_n$-heterocyclo;

R$_6$ and R$_6'$ are independently selected from the group consisting of lower alkyl, cycloalkyl, aryl, and heterocyclo;

m and m' are independently selected from the group consisting of zero and an integer from 1 to 5;

n is an integer from 1 to 5;

g is an integer from 2 to 5;

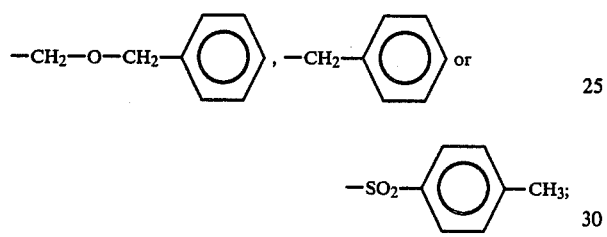

R$_8$ is 2,4-dinitrophenyl;

R$_9$ is hydrogen, lower alkyl, —(CH$_2$)$_m$-cycloalkyl, —(CH$_2$)$_m$-aryl, —(CH$_2$)n-heterocyclo,

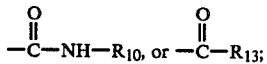

R$_{10}$ is hydrogen, lower alkyl, —(CH$_2$)$_m$-cycloalkyl, —(CH$_2$)$_m$-aryl, —(CH$_2$)$_n$-heterocyclo, or

R$_{13}$ is hydroxy, —O— lower alkyl, —O—(CH$_2$)$_m$-cycloalkyl, —O—(CH$_2$)$_m$-aryl, —O—(CH$_2$)$_n$-heterocyclo, or —NH$_2$;

q is zero or one;

the term lower alkyl refers to straight or branched chain radical having up to seven carbon atoms;

the term cycloalkyl refers to saturated rings of 4 to 7 carbon atoms;

the term halo refers to Cl, Br, and F;

the term halo substituted lower alkyl refers to such lower alkyl groups in which one or more hydrogens have been replaced by chloro, bromo or fluoro groups;

the term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are methyl, methoxy, methylthio, halogen or hydroxy; and the term heterocyclo refers to fully saturated or unsaturated rings of 5 or 6 atoms containing one to four N atoms, one O atom and up to two N atoms, or one S atom and up to two N atoms and bicyclic rings wherein the five or six membered ring containing O, S and N atoms as defined above is fused to a benzene ring.

2. A compound of claim 1 having the formula

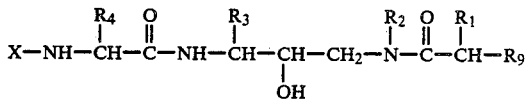

including a pharmaceutically acceptable salt thereof wherein:

X is lower

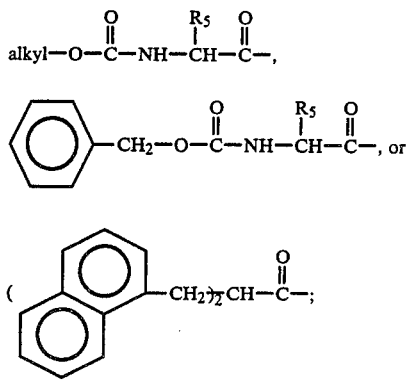

R$_1$ is hydrogen or lower alkyl of 1 to 5 carbons;

R$_2$ is hydrogen, lower alkyl of 1 to 5 carbons, —(CH$_2$)$_m$-cyclopentyl, —(CH$_2$)$_m$-cyclohexyl, or

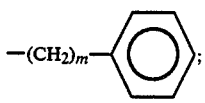

m is an integer from 1 to 3;

R$_3$ is straight or branched chain lower alkyl of 3 to 5 carbons, —CH$_2$-cyclopentyl, or —CH$_2$-cyclohexyl;

R$_4$ is

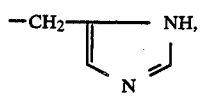

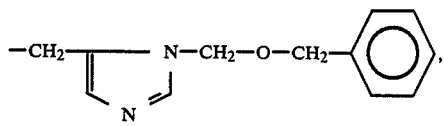

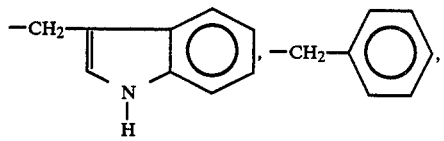

-continued

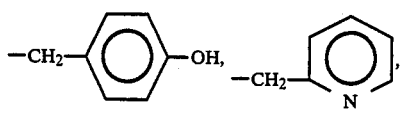

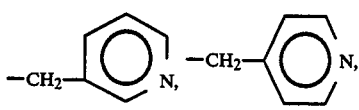

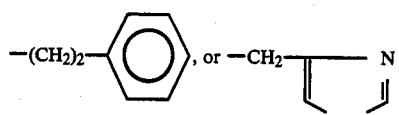

$R_5$ is

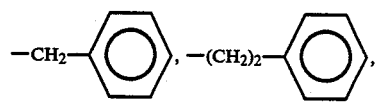

—$CH_2$-(α-naphthyl), —$CH_2$-(β-naphthyl),

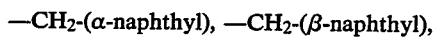

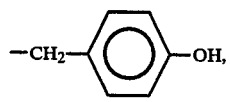

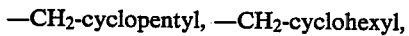

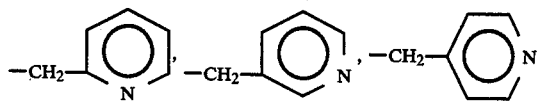

$R_9$ is lower alkyl of 1 to 5 carbons, —$(CH_2)_m$-cyclopentyl, —$(CH_2)_m$-cyclohexyl,

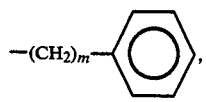

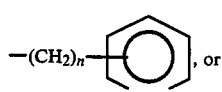, or

-continued

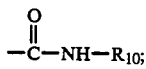—NH—$R_{10}$;

$R_{10}$ is lower alkyl of 1 to 5 carbons, —$(CH_2)_m$-cyclopentyl, —$(CH_2)_m$-cyclohexyl,

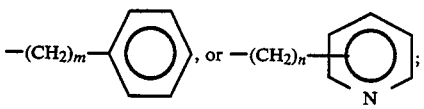

and n is an integer from 1 to 3.

3. A compound of claim 2 wherein:

X is

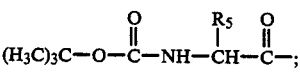

$R_1$ is hydrogen or —$(CH_2)_3$—$CH_3$;
$R_2$ is hydrogen, —$(CH_2)_4$—$CH_3$, or

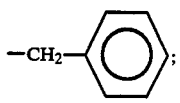;

$R_3$ is —$CH_2CH(CH_3)_2$ or —$CH_2$-cyclohexyl;
$R_4$ is

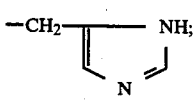

$R_5$ is

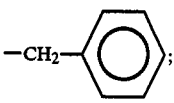;

and $R_9$ is —$(CH_2)_2$—$CH_3$;

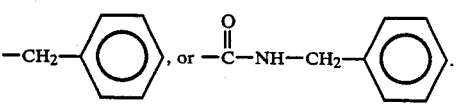

4. The compound of claim 3, $N^2$-[N-[(1,1-dimethylethoxy)carbonyl]-L-phenylalanyl]-N-[(S)-1-[1-hydroxy-2-[(1-oxopentyl)amino]ethyl]-3-methylbutyl]-L-histidinamide.

5. The compound of claim 3, $N^2$-[N-[(1,1-dimethylethoxy)carbonyl]-L-phenylalanyl]-N-[(S)-1-[1-hydroxy-2-[(1-oxo-3-phenylpropyl)-amino]ethyl]-3-methylbutyl]-L-histidinamide.

6. The compound of claim 3, $N^2$-[N-[(1,1-dimethylethoxy)carbonyl]-L-phenylalanyl]-N-[(S)-1-[1-hydroxy-2-[[1-oxo-2-[[(phenylmethyl)-amino]carbonyl]hexylamino]ethyl]-3-methyl-butyl]-L-histidinamide, hydrochloride (1:1.25).

7. The compound of claim 3, $N^2$-[N-[(1,1-dimethylethoxy)carbonyl]-L-phenylalanyl]-N-[(S)-1-[1-hydroxy-2-[(1-oxopentyl)pentylamino]-ethyl]-3-methylbutyl-L-histidinamide.

8. The compound of claim 3, $N^2$-[N-[(1,1-dimethylethoxy)carbonyl]-L-phenylalanyl]-N-[(S)-1-[1-hydroxy-2-[(1-oxo-3-phenylpropyl)-pentylamino]ethyl]-3-methylbutyl]-L-histidinamide.

9. The compound of claim 3, $N^2$-[N-[(1,1-dimethylethoxy)carbonyl]-L-phenylalanyl]-N-[(S)-1-[1-hydroxy-2-[(1-oxopentyl)(phenylmethyl)amino]ethyl]-3-methylbutyl]-L-histidinamide.

10. The compound of claim 3, N-[(1S)-1-(cyclohexylmethyl)-2-hydroxy-3-[1-oxo-2-[[(phenylmethyl)amino]carbonyl]hexyl]amino]-propyl]-$N^2$-[N-[(1,1-dimethylethoxy)carbonyl]-L-phenylalanyl]-L-histidinamide.

11. A composition for treating hypertension in a mammalian species comprising a pharmaceutically acceptable carrier and an antihypertensively effective amount of a compound of claim 1.

12. A method of treating hypertension in a mammalian species which comprises administering an antihypertensively effective amount of the composition of claim 11.

* * * * *